(12) United States Patent
Xie et al.

(10) Patent No.: US 8,691,947 B2
(45) Date of Patent: Apr. 8, 2014

(54) MATERIALS RELATED TO SODIUM/POTASSIUM ADENOSINE TRIPHOSPHATASE AND SRC

(75) Inventors: Zi-Jian Xie, Saline, MI (US); Qiqi Ye, Toledo, OH (US); Zhichuan Li, Toledo, OH (US)

(73) Assignee: The University of Toledo, Toledo, OH (US)

(*) Notice: Subject to any disclaimer, the term of this patent is extended or adjusted under 35 U.S.C. 154(b) by 0 days.

(21) Appl. No.: 13/521,871

(22) PCT Filed: Jan. 13, 2011

(86) PCT No.: PCT/US2011/021130
§ 371 (c)(1),
(2), (4) Date: Aug. 2, 2012

(87) PCT Pub. No.: WO2011/088210
PCT Pub. Date: Jul. 21, 2011

(65) Prior Publication Data
US 2013/0011335 A1   Jan. 10, 2013

Related U.S. Application Data

(60) Provisional application No. 61/294,665, filed on Jan. 13, 2010.

(51) Int. Cl.
*C07K 7/08* (2006.01)
*A61K 38/04* (2006.01)

(52) U.S. Cl.
USPC ........................................ 530/326; 514/21.4

(58) Field of Classification Search
None
See application file for complete search history.

(56) References Cited

U.S. PATENT DOCUMENTS

| | | | |
|---|---|---|---|
| 2,698,822 A | 1/1955 | Halpern et al. |
| 3,122,475 A | 2/1964 | Schaeppi |
| 3,687,944 A | 8/1972 | Pettit et al. |
| 4,261,971 A | 4/1981 | Appelgren et al. |
| 5,153,178 A | 10/1992 | Maroko |
| 5,888,527 A | 3/1999 | Nashimoto et al. |
| 6,113,965 A | 9/2000 | Goodsall et al. |
| 6,261,760 B1 | 7/2001 | Fielding et al. |
| 6,562,864 B1 | 5/2003 | Larson |
| 6,726,935 B2 | 4/2004 | Ji et al. |
| 7,157,493 B2 | 1/2007 | Zhao et al. |
| 7,195,783 B2 | 3/2007 | Shan et al. |
| 2002/0039764 A1 | 4/2002 | Rosen et al. |
| 2002/0055644 A1 | 5/2002 | Winter et al. |
| 2002/0091085 A1 | 7/2002 | Kay et al. |
| 2004/0229275 A1 | 11/2004 | Hayden et al. |
| 2005/0026849 A1 | 2/2005 | Singh et al. |
| 2006/0035835 A1 | 2/2006 | Taniyama et al. |
| 2006/0094772 A1 | 5/2006 | Chang et al. |
| 2006/0205679 A1 | 9/2006 | Streeper et al. |
| 2007/0092972 A1 | 4/2007 | Xiao et al. |
| 2007/0098765 A1 | 5/2007 | Zhao et al. |
| 2009/0082293 A1 | 3/2009 | Giordano et al. |
| 2009/0143279 A1 | 6/2009 | Mootha et al. |
| 2009/0226513 A1 | 9/2009 | Xie et al. |

FOREIGN PATENT DOCUMENTS

| | | |
|---|---|---|
| WO | 02/14343 A1 | 2/2002 |
| WO | 03/016475 A2 | 2/2003 |
| WO | 2004/004785 A1 | 1/2004 |
| WO | 2007/023011 A2 | 3/2007 |
| WO | 2007/089688 A2 | 8/2007 |
| WO | 2008/054792 A2 | 5/2008 |
| WO | 2010/053771 A1 | 5/2010 |
| WO | 2010/071767 A3 | 6/2010 |
| WO | 2011/034772 A1 | 3/2011 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Chinese Office Action, Application No. 200780043725.7 dated Jan. 12, 2011.
European Search Report, Application No. 0776299.6 dated Aug. 18, 2009.
European Supplementary Search Report, Application No. 07762999.6 dated Sep. 4, 2009.
PCT International Preliminary Report on Patentability, PCT/US09/067845 filed Dec. 14, 2009, dated Jun. 23, 2011.
PCT International Preliminary Report on Patentability, PCT/US07/002365 filed Jan. 30, 2007, dated Aug. 5, 2008.
PCT International Preliminary Report on Patentability, PCT/US07/023011 filed Oct. 31, 2007, dated May 14, 2009.
PCT International Preliminary Report on Patentability, PCT/US2009/062317 filed Oct. 28, 2009, dated May 12, 2011.

(Continued)

*Primary Examiner* — Zachary Howard
(74) *Attorney, Agent, or Firm* — MacMillan, Sobanski & Todd, LLC

(57) ABSTRACT

This invention is based in part on the elucidation of new structural conformations and functions of the sodium/potassium adenosine triphosphate synthase (Na/K ATPase), and especially elucidation of new binding sites and interactions. The present invention provides practical applications of several surprising structural and functional relationships between Na/K ATPase and compounds which interact with Na/K ATPase. Disclosure of these structures and relationships provides insight and practical solutions to chemically affecting not only the Na/K ATPase interactions, but also regulators known to be upstream and downstream.

3 Claims, 8 Drawing Sheets
(2 of 8 Drawing Sheet(s) Filed in Color)

(56) References Cited

OTHER PUBLICATIONS

PCT International Search Report and the Written Opinion, PCT/US07/02365 filed Jan. 30, 2007, dated Dec. 20, 2007.
PCT International Search Report and the Written Opinion, PCT/US07/23011 filed Oct. 31, 2007, dated Sep. 26, 2008.
PCT International Search Report and the Written Opinion, PCT/US09/62317 filed Oct. 28, 2009, dated Mar. 2, 2010.
PCT International Search Report and the Written Opinion, PCT/US09/67845 filed Dec. 14, 2009, dated Aug. 10, 2010.
PCT International Search Report and Written Opinion, PCT/US11/21127 filed Jan. 13, 2011, dated Apr. 13, 2011.
PCT International Search Report and Written Opinion, PCT/US11/21130 filed Jan. 13, 2011, dated Jun. 7, 2011.
Amigo, L. et al., "Enrichment of Canalicular Membrane with Cholesterol and Sphingomyelin Prevents Bile Salt-Induced Hepatic Damage," Journal of Lipid Research, 1999, pp. 533-542, vol. 40.
Aydemir-Koksoy, A. et al., "Ouabain-Induced Signaling and Vascular Smooth Muscle Cell Proliferation," The Journal of Biological Chemistry, 2001, pp. 46605-46611, vol. 276, No. 49.
Cai, T. et al., "Regulation of Caveolin-1 Membrane Trafficking by the Na/K-ATPase," Journal of Cell Biology, 2008, pp. 1153-1169, vol. 182, No. 6.
Chen, Y. et al., "Regulation of Intracellular Cholesterol Distribution by Na/K-ATPase," The Journal of Biological Chemistry, May 2009, pp. 14881-14890, vol. 284, No. 22.
Chen, Y., "The N-Terminus of a1 Subunit and Na/K-ATPase-Mediated Signal Transduction," Final Approval of Dissertation, The University of Toledo, College of Medicine, 2009.
Cooper, R. et al., "Medicinal Benefits of Green Tea: Part I. Review of Noncancer Health Benefits," The Journal of Alternative and Complementary Medicine, 2005, pp. 521-528, vol. '11, No. 3.
Cruz, J.C. et al., "Role of Niemann-Pick Type C1 Protein in Intracellular Trafficking of Low Density Lipoprotein-Derived Cholesterol," The Journal of Biological Chemistry, 2000, pp. 4013-4021, vol. 275, No. 6.
Darra, E. et al., "Protective Effect of Epigallocatechin-3-Gallate on Ischemia/Reperfusion-Induced Injuries in the Heart: STAT1 Silencing Flavenoid," Genes Nutr., 2007, pp. 307-310, vol. 2.
Dmitrieva, R.I. et al., "Cardiotonic Steroids: Potential Endogenous Sodium Pump Ligands with Diverse Function," Exp. Biol. Med., 2002, pp. 561-569, vol. 227, No. 8.
Elkareh, J. et al., "Marinobufagenin Stimulates Fibroblast Collagen Production and Causes Fibrosis in Experimental Uremic Cardiomyopathy," Hypertension, 2007, pp. 215-224, vol. 49.
El-Okdi, N. et al., "Effects of Cardiotonic Steroids on Dermal Collagen Synthesis and Wound Healing," J. Appl. Physiol., 2008, pp. 30-36, vol. 105.
Haas, M. et al., "SRC-Mediated Inter-Receptor Cross-Talk Between the Na+/K+-ATPase and the Epidermal Growth Factor Receptor Relays the Signal from Ouabain to Mitogen-Activated Protein Kinases," the Journal of Biological Chemistry, 2002, pp. 18694-18702, vol. 277, No. 21.
Hotta, Y. et al., "Positive Inotropic Effect of Purified Green Tea Catechin Derivative in Guinea Pig Hearts: The Measurements of Cellular Ca2+ and Nitric Oxide Release," European Journal of Pharmacology, 2006, pp. 123130, vol. 552.
Ikeda, I. et al., "Tea Catechins with a Galloyl Moiety Suppress Postprandial Hypertriacylglycerolemia by Delaying Lymphatic Transport of Dietary Fat in Rats," the Journal of Nutrition, 2005, pp. 155-159, vol. 135.
Kabat, M.M. et al., "Cardiotonic Steroids. 5. A Synthesis of Bufadienolides and Cardenolides from 3β-Acetoxy-5-Androsten-17-One via Common Intermediates," J. Org. Chem., 1983, pp. 4248-4251, vol. 48.
Katz, B. et al., "Controlled-Release Drug Delivery Systems in Cardiovascular Medicine," American Heart Journal, 1995, pp. 359-368, vol. 129, No. 2.
Kennedy, D.J. et al., "Central Role for the Cardiotonic Steroid Marinobufagenin in the Pathogenesis of Experimental Uremic Cardiomyopathy," Hypertension, 2006, pp. 488-495, vol. 47.
Khundmiri, S.J. et al., "Ouabine Induces Cell Proliferation through Calcium-Dependent Phosphorylation of Akt (Protein Kinase B) in Opossum Kidney Proximal Tubule Cells," Am. J. Physiol. Cell Physiol., 2006, pp. C1247-C1257, vol. 291.
Kubota, Y. et al., "Safety of Dietary Supplements; Chronotropic and Inotropic Effects on Isolated Rat Atria," Biol. Pharm Bull., 2002, pp. 197-200, vol. 25, No. 2.
Laird, A.D. et al., "Src Family Kinase Activity is Required for Signal Tranducer and Activator of Transcription 3 and Focal Adhesion Kinase Phosphorylation and Vascular Endothelial Growth Factor Signaling in Vivo and for Anchorage-Dependent and -Independent Growth of Human Tumor Cells," Molecular Cancer Therapeutics, May 2003, pp. 461-469, vol. 2.
Lefranc, F. et al., "Targeting the α1 Subunit of the Sodium Pump to Combat Glioblastoma Cells," Neurosurgery, Jan. 2008, pp. 211-222, vol. 62, No. 1.
Liang, M. et al., "Functional Characterization of Src-Interacting Na/K-ATPase Using RNA Interference Assay," The Journal of Biological Chemistry, Jul. 2006, pp. 19709-19719, vol. 281, No. 28.
Newman, R.A. et al., "Cardiac Glycosides as Novel Cancer Therapeutic Agents," Molecular Interventions, Feb. 2008, pp. 36-49, vol. 8, Issue 1.
Paquay, J.B.G. et al., "Protection Against Nitric Oxide Toxicity by Tea," J. Agric. Food Chem., 2000, pp. 5768-5772, vol. 48.
Robia, S.L. et al., "Localization and Kinetics of Protein Kinase C-Epsilon Anchoring in Cardiac Myocytes," Biophysical Journal, May 2001, pp. 2140-2151, vol. 80.
Sato, A. et al., "α-Mangostin Induces Ca2+-ATPase-Dependent Apoptosis via Mitochondrial Pathway in PC12 Cells," Journal of Pharmacological Sciences, 2004, pp. 33-40, vol. 95.
Susa, M. et al., "Src Inhibitors: Drugs for the Treatment of Osteoporosis, Cancer or Both?" TiPS, 2000, pp. 489-495, vol. 21.
Tian, J. et al., "Binding of Src to Na+/K+ATPase Forms a Functional Signaling Complex," Molecular Biology of the Cell, Jan. 2006, pp. 317-326, vol. 17.
Tian, J. et al., "Changes in Sodium Pump Expression Dictate the Effect s of Ouabine on Cell Growth," the Journal of Biological Chemistry, May 2009, pp. 14921-14929, vol. 284, No. 22.
Tian, J. et al., "Na/K-ATPase Moonlights via Ouabine-Regulated Interaction with Src," Abstract, The FASEB Journal, Mar. 2004, vol. 18, No. 5.
Townsend, P.A. et al., "Epigallocatechin-3-Gallate Inhibits Stat-1 Activation and Protects Cardiac Myocytes from Ischemia/Reperfusion-Induced Apoptosis," The Faseb Journal, 2004, doi: 10.1096/fj.04-1716fje.
Urano, Y. et al., "Transport of LDL-Derived Cholesterol from the NPC1 Compartment to the ER Involves the Trans-Golgi Network and the SNARE Protein Complex," PNAS, Oct. 2008, pp. 16513-16518, vol. 105, No. 43.
Wang, H., "Na+/K+ATPase and Signal Transduction," Final Approval of Dissertation, The University of Toledo, College of Medicine, 2005.
Zhang, Z. et al., "Identification of Hyroxyxanthones as Na/K-ATPase Ligands," Molecular Pharmacology, 2010, pp. 961-967, vol. 77, No. 6.

* cited by examiner

YFP stable clone- YFP Ctrl  YFP-CD2 stable clone-CD2-2

Cell growth curve of CD2 clones vs. control cell lines

MATERIALS RELATED TO SODIUM/POTASSIUM ADENOSINE TRIPHOSPHATASE AND SRC

CROSS-REFERENCE TO RELATED APPLICATIONS

This application claims the benefit of PCT application No. PCT/US2011/021130 filed Jan. 13, 2011 which claims priority to U.S. Provisional Application Ser. No. 61/294,665 filed on Jan. 13, 2010, the entire disclosure of which is expressly incorporated herein by reference.

STATEMENT REGARDING FEDERALLY SPONSORED RESEARCH

This invention was made with government support under Grant Numbers HL-36573 and HL-67963 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jan. 13, 2011, is named 420_52651_SEQ_LIST_D2010-28.txt and is 527 bytes in size.

FIELD OF THE INVENTION

This invention pertains to the field of biology, chemistry and medicine. The invention specifically pertains to ion transport proteins, small pharmaco-active molecules, research tools, diagnostics, kits and treatments related to cardiovascular diseases. Cardiotonic steroid antagonists and compositions affecting cholesterol-mediated cardiovascular disease are within the field of the invention. Other fields, such as physics and biochemistry also provide a framework for the present invention.

BACKGROUND OF THE INVENTION

This invention is based in part on the elucidation of new structural conformations and functions of the sodium/potassium adenosine triphosphate synthase (Na/K ATPase), and especially elucidation of new binding sites and interactions. The present invention provides applications of surprising structural and functional relationships between Na/K ATPase and compounds which interact with Na/K ATPase. The invention provides solutions to chemically affecting not only the Na/K ATPase interactions, but also regulators known to be upstream and downstream.

Sodium and potassium transport activity across the cell membrane is intrinsically related to many cellular processes including metabolism, gene expression and cell growth. The Na/K-ATPase is highly expressed and represents one of the most fundamentally important proteins of animal physiology. Moreover, the expression and the activity of Na/K-ATPase are important in regulation of the overall transport activity of a cell. This so-called pump/leak coupling exists in almost every mammalian cell. Because protein phosphorylation constitutes a pivotal mechanism by which the cellular processes are coordinated, the inventors postulate the existence of a receptor mechanism that can couple the transmembrane transport activity of Na/K-ATPase to on/off of protein kinases.

It is known that a large number of Na/K-ATPase interacts directly with Src kinase in cultured cells as well as in vivo. The interaction involves at least two pairs of protein domains. Specifically, the second cytosolic domain of α1 subunit (CD2) interacts with the Src SH2 and the nucleotide binding (N) domain associates with the Src kinase domain. The latter interaction keeps Src in an inactive state and binding of cardiotonic steroids such as ouabain to the Na/K-ATPase/Src complex activates the associated Src, resulting in the assembly and activation of various protein kinase cascades.

SUMMARY OF THE INVENTION

The present invention provides composition of matter comprising an amino acid compound comprising at least ten consecutive amino acid residues of the sequence STNCV EGTAR GIVVY TGD [SEQ ID NO:1], or conservative substitutions of the at least ten consecutive amino acid residues, wherein the compound is capable of binding the SH2 domain of Src.

Preferred are those compositions, which further comprise a therapeutically acceptable excipient. Most preferred are those wherein the amino acid compound comprises the sequence STNCV EGTAR GIVVY TGD [SEQ ID NO: 1].

Also preferred are those which bind to Src with an $IC_{50}$ selected from the group consisting of: less than about 90 nM; less than about 75 nM; less than about 50 nM; less than about 40 nM; less than about 30 nM, less than about 20 nM; less than about 10 nM; and less than 7 nM.

Also provided are nucleic acid compounds encoding a composition herein, as are vectors, and cells, particularly *E. coli* and mammalian cells, particularly tumor cells.

Also provided are monoclonal antibodies selective for a composition herein, preferably those which further comprise a detectable label selected from the group consisting of: radioactive label; chemical label; fluorescent label; an antibody; and a protein. Preferred are those compositions herein wherein the composition is capable of affecting a cellular process selected from the group consisting of: antagonizing a CTS-induced protein kinase cascade; upregulating a CTS induced protein kinase cascade; Src inhibition; Src stimulation; Na/K-ATPase mimic; Na/K-ATPase competitive inhibitor; Lyn inhibition; Lyn stimulation; ouabain antagonism; ouabain stimulation; ERK1/2 activation; ERK1/2 inhibition; membrane permeability by sodium ions; membrane permeability by potassium ions.

Also preferred are those compositions herein which further comprise at least one additional therapeutic composition useful to a treat a disease selected from the group consisting of: cancer; vascular disease; cardiovascular disease; heart disease; prostate cancer; breast cancer; neuroblastoma; cardiac hypertrophy; tissue fibrosis; congestive heart failure; ischemia/reperfusion injury; and Src-related diseases.

Also preferred are those compositions herein which further comprise a second compound bound with the amino acid compound in a location other than SEQ ID NO: 1, wherein the second compound is selected from the group consisting of: chemotherapeutic drug; toxin; immunological response modifier; enzyme; and radioisotope.

In other broad embodiments, there are provided methods to bind a compound to the SH2 domain of in vitro, comprising contacting a compound herein to at least one SH2 domain of Src. Preferred are those methods to bind a compound to the SH2 domain of Src in a Src-expressing cell, comprising contacting a compound of herein to at least one Src-expressing cell. More preferred are those methods wherein the Src-expressing cell is a mammalian cell, particularly a monocyte, heart cell, liver cell, vascular cell; breast cell; prostate cell; kidney cell; muscle cell; blood cell; and brain cell. In vitro and in vivo methods are preferred, particularly animal models, particularly mouse and humans.

Also provided are methods of treating a Src-associated disease in a mammal in need of such treatment, comprising administering a therapeutic composition herein. In particular, preferred are those methods wherein the Src-associated disease is selected from the group consisting of: cancer; vascular disease; cardiovascular disease; heart disease; prostate cancer; breast cancer; neuroblastoma; cardiac hypertrophy; tissue fibrosis; congestive heart failure; and ischemia/reperfusion injury. Methods for treating mammals, particularly those wherein the mammal is human, are preferred.

Also provided are methods for treating cancer in a mammal in need of such treatment, comprising administering a Src-inhibiting therapeutic composition herein.

Also provided are methods for vascular disease in a mammal in need of such treatment, comprising administering a Src-inhibiting therapeutic composition herein.

Also provided are methods for cardiovascular disease in a mammal in need of such treatment, comprising administering a Src-inhibiting therapeutic composition herein.

Also provided are methods for heart disease in a mammal in need of such treatment, comprising administering a Src-inhibiting therapeutic composition herein.

Also provided are methods for treating prostate cancer in a mammal in need of such treatment, comprising administering a Src-inhibiting therapeutic composition herein.

Also provided are methods for treating breast cancer in a mammal in need of such treatment, comprising administering a Src-inhibiting therapeutic composition herein.

Also provided are methods for treating neuroblastoma in a mammal in need of such treatment, comprising administering a Src-inhibiting therapeutic composition herein.

Also provided are methods for treating cardiac hypertrophy in a mammal in need of such treatment, comprising administering a Src-inhibiting therapeutic composition herein.

Also provided are methods for treating tissue fibrosis in a mammal in need of such treatment, comprising administering a Src-inhibiting therapeutic composition herein.

Also provided are methods for treating congestive heart failure in a mammal in need of such treatment, comprising administering a Src-stimulating therapeutic composition herein.

Also provided are methods for ischemia/reperfusion injury in a mammal in need of such treatment, comprising administering a Src-stimulating therapeutic composition herein.

Also provided are methods for reducing increased basal Src activity in a tumor cell, comprising administering a Src-inhibiting composition herein to a Src-expressing tumor cell.

Also provided are methods for affecting FAK in a tumor cell comprising administering a Src-inhibiting composition herein to a Src-expressing tumor cell, particularly wherein the Src-expressing cell is a TCN cell.

Also provided are methods for reducing tumor cell migration in a tumor cell test model, comprising administering a Src-inhibiting composition of claim 1 to a Src-expressing tumor cell.

Also provided are methods for killing cancer cells when the expression of Na/K ATPase is reduced, comprising administering a Src-inhibiting composition herein to a Src-expressing tumor cell having reduced Na/K ATPase expression.

Also provided are methods for inhibiting cell growth in a tumor cell line, comprising administering a Src-inhibiting composition herein to a Src-expressing tumor cell line, particularly which further comprises comparison of the ability of a composition herein to inhibit cell growth in a tumor cell line to a test compound's ability to inhibit cell growth in the same tumor cell line.

Also provided are methods for inhibiting prostate tumor cell growth in a prostate tumor cell line, comprising administering a Src-inhibiting composition herein to a Src-expressing prostate tumor cell line, particularly which further comprises comparison of the ability of a composition of claim 1 inhibiting prostate tumor cell growth in a prostate tumor cell line to a test compound's ability to inhibit cell growth in the same prostate tumor cell line.

Also provided are methods for inhibiting breast tumor cell growth in a breast tumor cell line, comprising administering a Src-inhibiting composition herein to a Src-expressing breast tumor cell line, particularly which further comprises comparison of the ability of a composition of claim 1 inhibiting prostate tumor cell growth in a breast tumor cell line to a test compound's ability to inhibit cell growth in the same breast tumor cell line.

Also provided are methods for inhibiting neuroblastoma cell growth in a neuroblastoma tumor cell line, comprising administering a Src-inhibiting composition of claim 1 to a Src-expressing neuroblastoma tumor cell line, particularly which further comprises comparison of the ability of a composition of claim 1 inhibiting neuroblastoma tumor cell growth in a prostate tumor cell line to a test compound's ability to inhibit cell growth in the same neuroblastoma tumor cell line.

Also provided are methods for screening at least one test composition to determine whether the at least one composition affects Src, comprising: introducing a test composition comprising a modified amino acid compound of STNCV EGTAR GIVVY TGD [SEQ ID NO: 1] to Src, wherein the modification is at least one conservative amino acid substitution; and determining whether the test composition affects Src.

Preferred are methods as described above, wherein the affect is selected from the group consisting of: Src binding; Src inhibition; Src stimulation; Src function; Lyn binding; Lyn function; Lyn inhibition; ouabain antagonism; Na/K-ATPase function; ERK1/2 function; FAK inhibition; membrane permeability by sodium ions; membrane permeability by potassium ions. Also preferred are those methods as above, wherein introducing a test composition is accomplished in vitro, in at least one mammalian cell, and/or in at least one tumor cell line. Also preferred are those methods as above, wherein determining whether the composition affects Src is measured by cell growth compared to control, by tumor growth compared to control, and/or by cell migration compared to control, preferably in an animal model, most preferably in a NOD/SCID mouse and/or a human.

Also provided are methods to screen for test compositions capable of inhibiting binding between CD2 domain of Na/K ATPase and SH2 domain of Src, comprising the steps of: a. incubating test compositions with purified Src for at least 5 and up to 45 minutes in a vessel; b. introducing Na/K ATPase to the vessel for at least 5 minutes and up to 45 minutes; c. introducing ouabain to the vessel for at least 1 minute and up to 45 minutes; d. introducing Mg2+/ATP to the vessel for at least 0.5 minute and up to 45 minutes; e. conducting western blot analysis to determine if Src activation was induced by ouabain. Preferred are such methods, wherein steps a. and b. are each 12-17 minutes, step c. is 2 to 7 minutes, and step d. is at least one minute.

Also provided are methods to screen for test compositions capable of inhibiting binding between CD2 domain of Na/K ATPase and SH2 domain of Src, comprising the steps of: a. contacting a test composition with a FRET pair of CD2 domain and SH2 domain; and b. identifying those compositions which abolish the FRET energy as capable of inhibiting the CD2/SH2 interaction. Preferred are those methods, wherein the CD2 is labeled with Cy3 and the SH2 is labeled with Cy5, particularly via incubation in a 96 well plate, and most particularly, the FRET energy is measured using a spectra meter.

Various aspects of this invention will become apparent to those skilled in the art from the following detailed description of the preferred embodiment, when read in light of the accompanying drawings.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 1A: GST pull-down analyses showing the concentration-dependent interaction between Src and two domains of α1 subunit. The purification of different constructs and the pull-down analyses were performed as previously described. Upper panel showed a representative Western blot. Lower panel showed the Commassie blue staining of GST, GST-CD2, and GST-ND1. n=3.

FIG. 1B: Modeling of Na/K-ATPase/Src interaction. Modeling of E1 and E2 Na/K-ATPase was based on SERCA1a structure file 1SU4 and Na/K-ATPase structure file 2zxe, and generated using SPDBView V3.7 program. The A domain (N-terminus and CD2) in the α1 subunit was labeled in sky blue, P domain in green, N domain in red. The SH2 domain of Src was labeled in purple, kinase domain in blue.

FIG. 2 A and FIG. 2B: Regulation of the Na/K-ATPase-associated Src by chemical modifiers. The Na/K-ATPase was purified from pig kidney and the purified Src was purchased from Upstate. To stabilize the Na/K-ATPase in the E2P conformation, the purified Na/K-ATPase was treated by two different fluoride compounds (BeF and AlF) as described, washed and then incubated with Src. The ouabain-treated and control Na/K-ATPase/Src complex was used as positive and negative controls for the experiments, respectively. Similarly, the Na/K-ATPase was stabilized at the E1P state by NEM/AMPPNP as described and then analyzed.

FIG. 3A, FIG. 3B and FIG. 3C: Effects of Na$^+$ and K$^+$ on the Na/K-ATPase-associated Src. The purified Na/K-ATPase was incubated with the purified Src in the presence of different ligands for 15 min, and assayed for Tyr418 phosphorylation as in FIG. 2. Representative Western blots are shown under each experimental condition. Quantitative data were presented as mean±S.E. of at least three independent experiments.

FIG. 3D: Effects of extracellular K+ on Src in LLC-PK1 cells. Cells were exposed to the normal medium (K$^+$ 5 mM) or low K$^+$ (K$^+$ 1 mM) medium, and then stained for Tyr(P)$^{418}$ Src as described. The scale bar represents 20 μm.

FIG. 3E, FIG. 3F, and FIG. 3G: Cells were exposed to media containing different concentrations of K$^+$ or Na$^+$, and then lysed. Cell lysates were subjected to Western blot analyses of Src and ERKs as indicated. Quantitative data was presented as mean±S.E. of at three independent experiments. *, $p<0.05$; **, $p<0.01$.

FIG. 7. CD2C2 Peptide as a Novel Ouabain Antagonist.

DETAILED DESCRIPTION OF THE INVENTION

The Na/K-ATPase undergoes E1/E2 conformational transition during an ion pumping cycle. A large number of cellular Na/K-ATPase also interacts with Src kinase via two pairs of domains. While the Na/K-ATPase actuator domain binds the Src SH2 domain with a higher affinity than that between the nucleotide binding domain and the Src kinase domain, the latter keeps Src in an inactive state. The E1 Na/K-ATPase could bind both the SH2 and kinase domains simultaneously and that the transition from the E1 to E2 would release the kinase domain, resulting in the activation of the Na/K-ATPase-associated Src. Indeed, the inventors demonstrate this conformation-dependent regulation of Src using purified enzyme preparations. Consistently, cellular conditions that increase the formation of the E2 Na/K-ATPase stimulate cellular Src activity and the down-stream protein kinase cascades in live cells. Taken together, these discoveries now show a previously unrecognized signaling mechanism that may couple the change in conformational states of Na/K-ATPase to activation/inhibition of cellular protein kinase cascades.

Figure 1A:
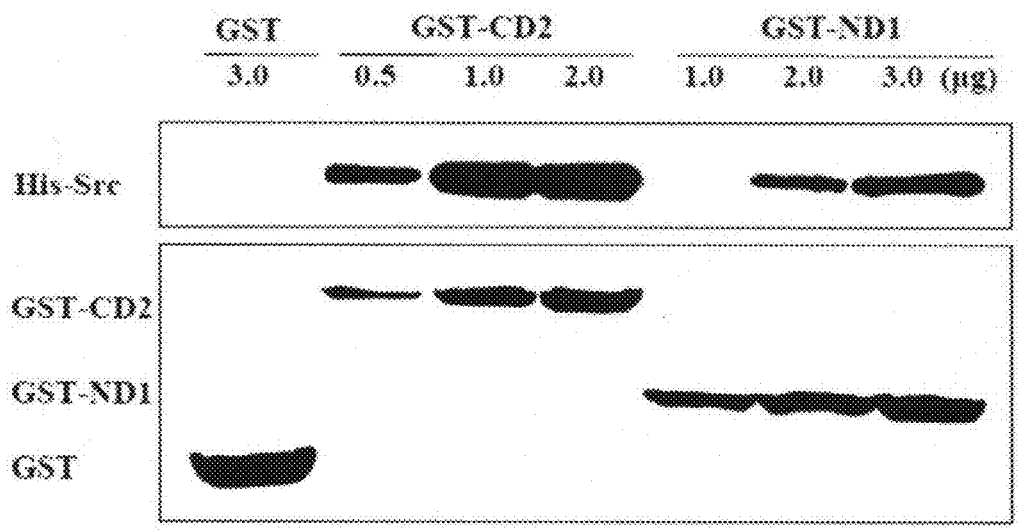
FIGS. 1A-1B. The interaction between the Na/K-ATPase and Src.
Figure 1B:
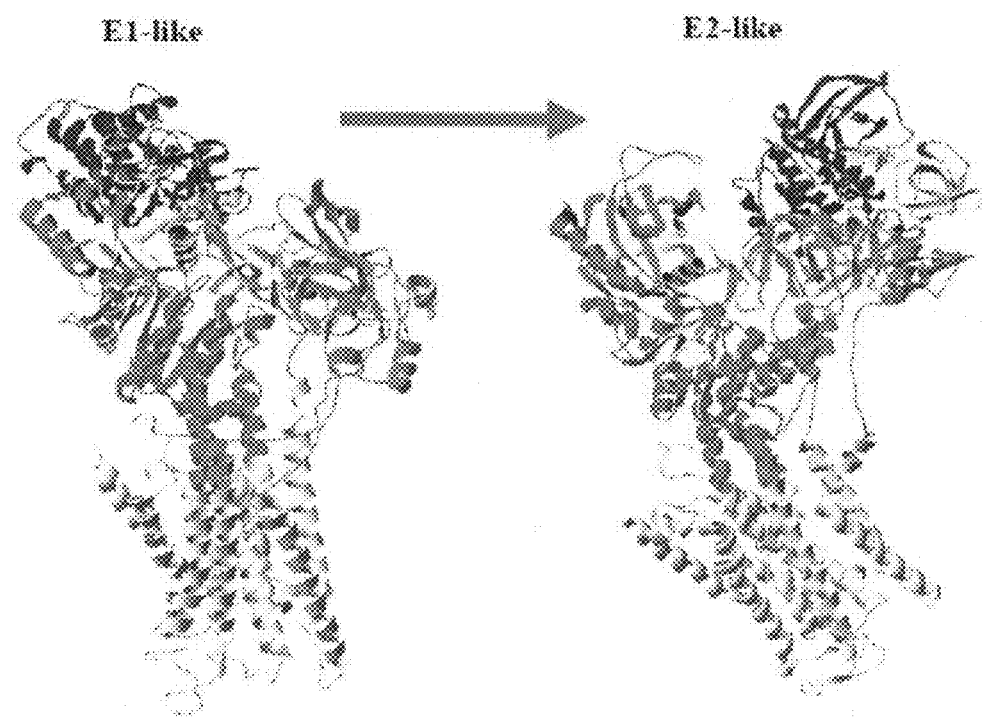

Based on the crystal structure of Na/K-ATPase, the CD2 constitutes a part of the actuator (A) domain. As depicted in FIG. 1A, the interaction between the A and SH2 domain exhibits higher affinity than that of N domain/kinase domain interaction. Moreover, the inventors' in vitro binding data indicate that the Na/K-ATPase is likely to interact with both the SH2 and kinase domains simultaneously in the absence of ouabain. During the pumping cycle, the Na/K-ATPase undergoes E1 to E2 conformational transition where the N domain closes up and the A domain rotates to dock onto the N and P domains. Structure modeling suggests that the location of and the space between the A and N domains at the E2 state are unlikely to allow the α1 subunit to bind both the SH2 and the kinase domains simultaneously (FIG. 1B).

Because the Src binding, even at the molar ratio of 1:1, exhibits no significant effect on Na/K-ATPase activity (FIG. 5), the inventors now believe that the Na/K-ATPase could exert a conformation-dependent regulation of Src. Specifically, as illustrated in FIG. 1B, while the E1 Na/K-ATPase inhibits Src, the E2 Na/K-ATPase would release the kinase domain, resulting in the activation of Na/K-ATPase-associated Src. The rotation of A domain may be sufficient and necessary to push the kinase domain off the moving N domain during the E1 to E2 transition of the Na/K-ATPase, resulting in the activation of Src.

The inventors utilized different chemical modifiers to stabilize the Na/K-ATPase in distinct conformational states and then assessed the conformation-dependent effect of Na/K-ATPase on Src. Fluoride compounds such as aluminum fluoride and beryllium fluoride, can interact with Na/K-ATPase as phosphate analogues, and stabilize the enzyme as well as other P-type ATPase in the E2P conformation. Thus, to demonstrate the stimulatory effect of E2 Na/K-ATPase on Src activity, the inventors prepared AIF- and BeF—Na/K-ATPase and measured their effects on Src.

Figure 2A:
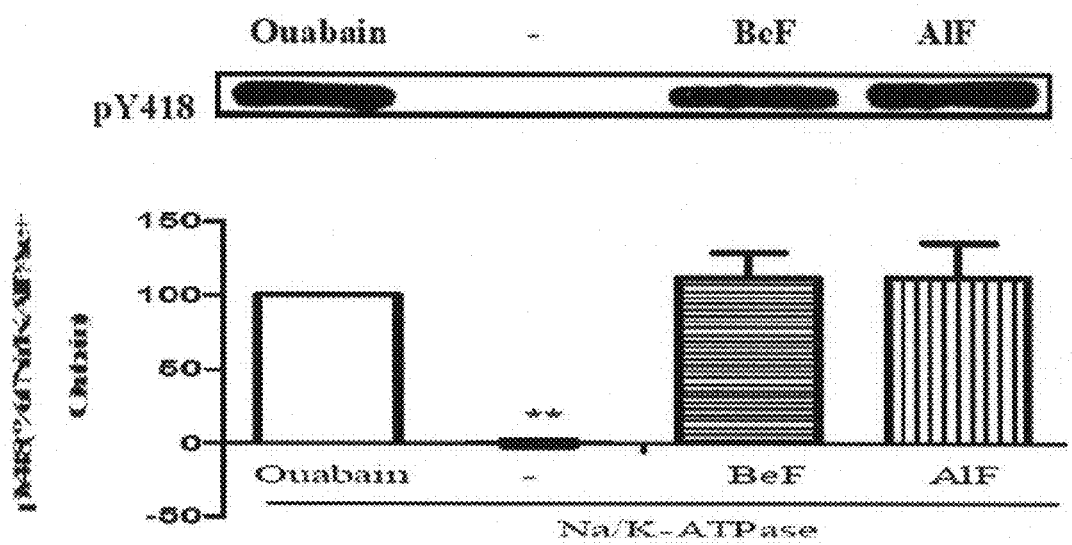
FIGS. 2A-2B. The E1 and E2-dependent regulation of Src by the Na/K-ATPase.
Figure 2B:
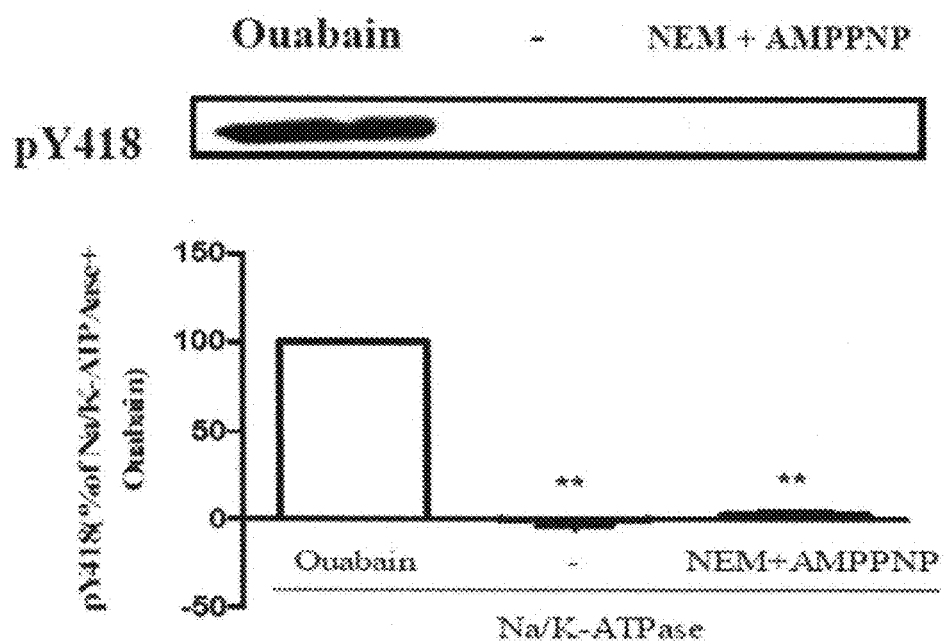

As depicted in FIG. 2A, like ouabain, treatment of the Na/K-ATPase with either aluminum fluoride or beryllium fluoride was sufficient to stimulate the Na/K-ATPase-associated Src. On the other hand, when the Na/K-ATPase is stabilized in E1P by N-ethylmaleimide (NEM) and a slowly hydrolysable ATP analogue adenyl-5'-yl imidodiphosphate (AMP-PNP), the Na/K-ATPase-associated Src is completely inhibited (FIG. 2B). As a control, the inventors also assessed whether these chemical modifiers have direct effect on Src. No significant effect was observed under the same experimental conditions (data not shown).

The existence of E1 and E2 conformations of the Na/K-ATPase during the catalytic cycle was first detected as distinct patterns of proteolytic cleavage in either $Na^+$ or $K^+$ medium. In the presence of $Na^+$, chymotrypsin cleaves E1 Na/K-ATPase at Leu-266 in the A domain, producing an 83 kDa fragment. While the 83 kDa peptide retains the ability to form phosphoenzyme intermediate (EP), the chymotrypsin cleavage disrupts the coordinated movement of A and N domains, resulting in a complete inhibition of the ATPase activity. Thus, if the coordinated movement of A and N domain is required for the conformation-dependent activation of the Na/K-ATPase-associated Src as depicted in FIG. 1B, the inability of A domain to push off the Src kinase domain from the N domain would cause a complete inhibition of Src.

Figure 2C:
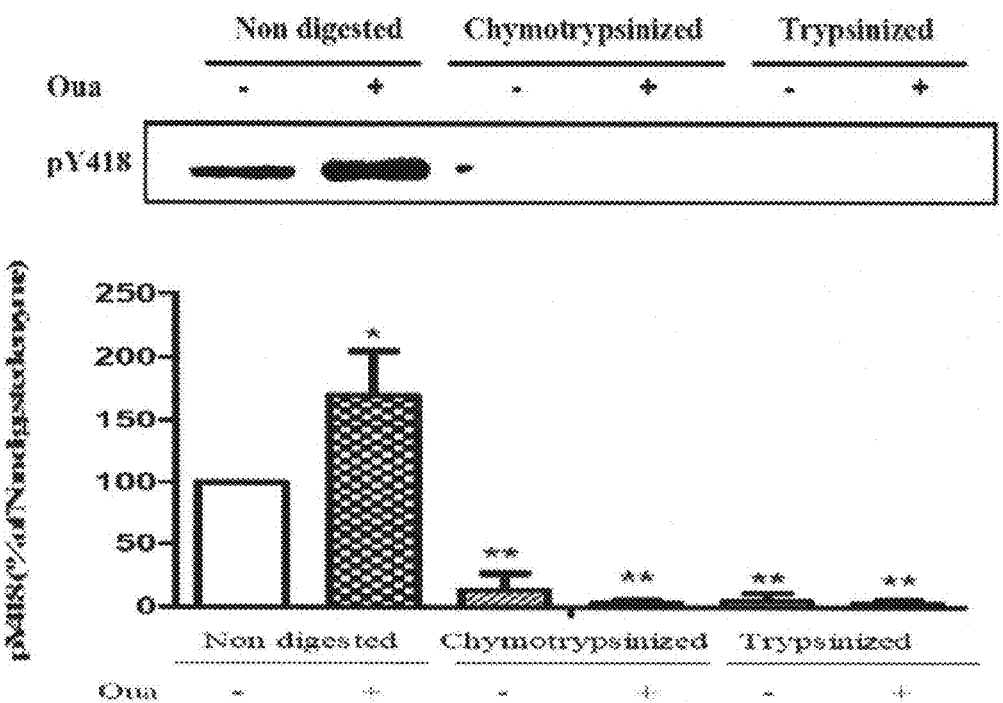
FIG. 2C, effects of chymotrypsin and trypsin digestion on Na/K-ATPase-mediated Src regulation. The purified Na/K-ATPase was subjected to chymotrypsin or trypsin digestion as described. The digested enzyme was washed and assayed for Na/K-ATPase activity. The enzyme preparations with less than 25% activity was incubated with Src in 150 mM Na$^+$ medium in the presence or absence of 10 μM ouabain. The non-digested enzyme was used as control. The activity of Src was measured, and a representative Western blot was shown under each experimental condition. Quantitative data was presented as mean±S.E. of at least 3 separate experiments. *, $p<0.05$; **, $p<0.01$.

Indeed, as depicted in FIG. 2C, while $Na^+$ (lane 1) and ouabain (lane 2) were able to stimulate the Na/K-ATPase-associated Src, they failed to do so after the Na/K-ATPase was digested by chymotrypsin in the presence of $Na^+$. To further confirm the importance of coordinated movement of A and N domain, the E2 Na/K-ATPase was digested by trypsin in the presence of $K^+$, washed, and then subjected to the same assay. Unlike chymotrypsin, trypsin cleaves E2 Na/K-ATPase at Arg-438 in the N domain, producing a 48 kDa fragment that retains the capability of forming EP. However, like chymotrypsin digestion, disruption of the coordinated movement of A and N domains by trypsin was equally effective in inhibiting $Na^+$ and ouabain-induced activation of Src.

Figure 3A:
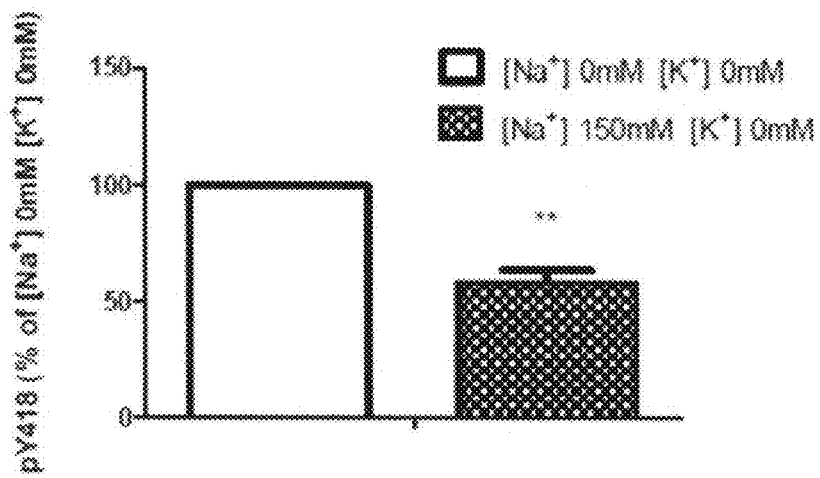
FIGS. 3A-3G. Regulation of Na/K-ATPase-associated Src by different ions.
Figure 3B:
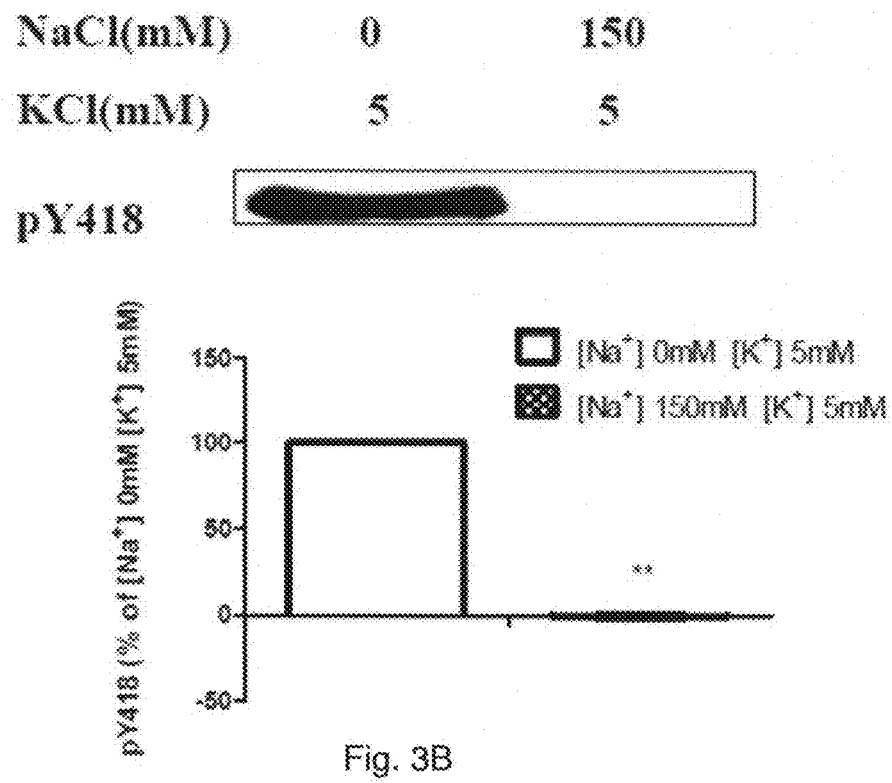
Figure 3C:
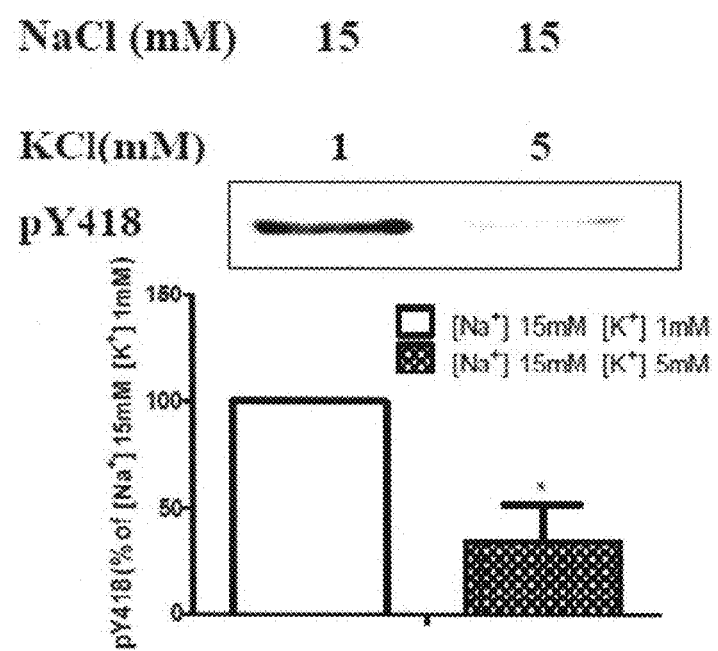

The above in vitro studies indicate that the Na/K-ATPase can turn Src on/off through coordinated movements of A and N domains during E2/E1 conformational transition. To verify the above findings and assess the physiological relevance of this conformation-dependent regulation of Na/K-ATPase-associated Src, the inventors incubated the purified Na/K-ATPase/Src complex in the presence of different ions that are known to alter the formation of E1/E2 Na/K-ATPase. In comparison to choline, $Na^+$ was more potent in converting E2 conformation to E1. Accordingly, addition of 150 mM $Na^+$ to the reaction buffer caused a partial inhibition of Src (FIG. 3A). Moreover, in the presence of both $Na^+$ and $K^+$, the addition of ATP-$Mg^{2+}$ would favor the formation of E1 Na/K-ATPase and produced a further inhibition of Src (FIG. 3B). However, removal of $Na^+$ from this reaction buffer would increase the formation of E2 Na/K-ATPase. Consistently, it stimulated the Na/K-ATPase-associated Src (FIG. 3B). Physiologically, the cellular Na/K-ATPase is exposed to about 15 mM $Na^+$ intracellularly and 5 mM $K^+$ extracellularly. Under these ionic conditions, the inventors saw that most of Na/K-ATPase-associated Src was inactive. Lowering $K^+$ from 5 mM to 1 mM produced a robust stimulation of Na/K-ATPase-associated Src (FIG. 3C). Taken together, these findings now show that the Na/K-ATPase-associated Src can be regulated by the substrate-induced conformational changes.

The above shows that Na/K-ATPase may control Src activity through substrate-induced E1/E2 transitions. Because the balance of E1/E2 Na/K-ATPase in live cells can be regulated by extracellular $K^+$ and intracellular $Na^+$, to further explore the physiological significance of this E1/E2-mediated Src regulation, the inventors measured Src activity in LLC-PK1 cells after the cells were exposed to different concentrations of extracellular $K^+$. Lowering extracellular $K^+$ would slow down the dephosphorylation of E2P and accumulate E2 Na/K-ATPase in live cells.

Figure 3D:
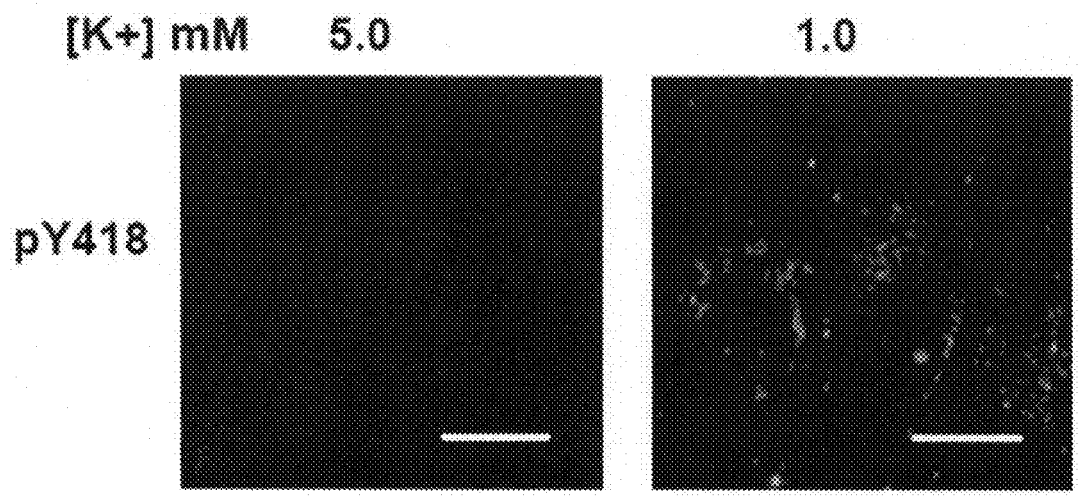
Figure 3E:
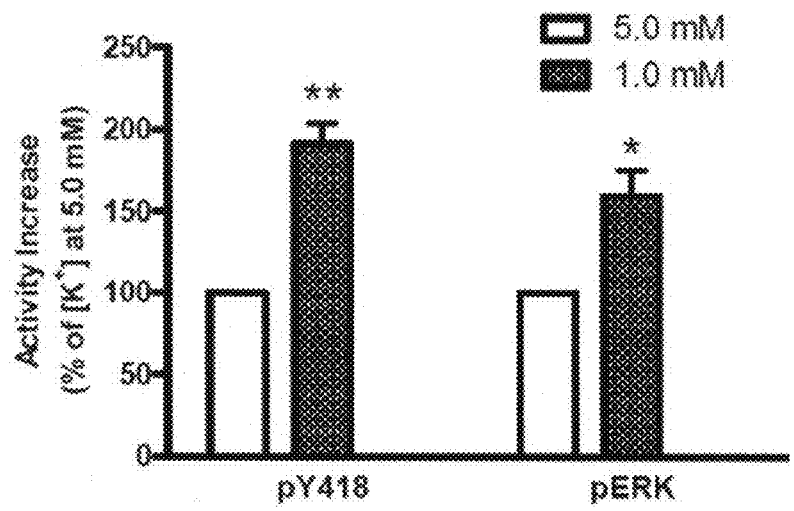

As depicted in FIG. 3D, confocal imaging analyses showed that lowering extracellular $K^+$ from 5 mM to 1 mM significantly increased cellular contents of active Src in LLC-PK1 cells, consistent with the findings depicted in FIG. 3C. To verify these findings, the inventors also conducted Western blot analyses of cell lysates after the cells were incubated in normal or low $K^+$ medium. As shown in FIG. 3E, lowering $K^+$ from 5 mM to 1 mM, like addition of ouabain, not only stimulated cellular Src activity, but also the down-stream kinase cascade of ERKs.

To verify that the Na/K-ATPase/Src complex is the receptor for low $K^+$-induced signal transduction in LLC-PK1 cells, the inventors repeated the above experiments in Na/K-ATPase-knock down PY-17 cells. PY-17 cells are derived from LLC-PK1 cells that were transfected with plasmids expressing α1-specific siRNA. In comparison to P-11 cells, PY-17 cells express about 10% of α1 and have reduced number of Na/K-ATPase/Src complex.

Figure 3F:
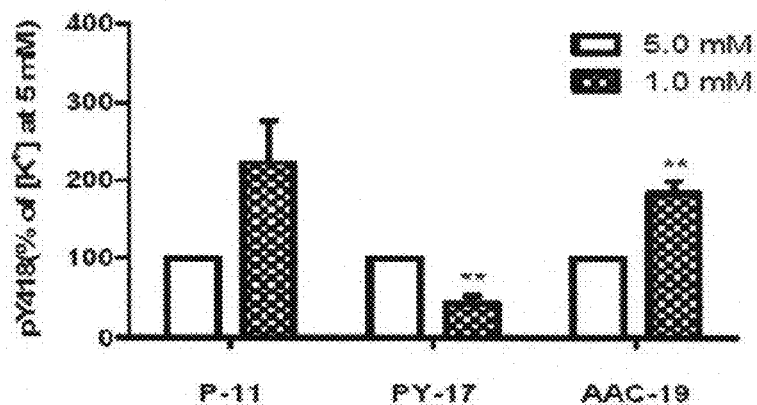

As shown in FIG. 3F, lowering extracellular $K^+$ from 5 to 1 mM failed to increase cellular Src activity in PY-17 cells, indicating that the formation of Na/K-ATPase/Src complex is required for low $K^+$ to stimulate cellular Src activity. This notion is further supported by the fact that rescuing PY-17 cells by knock-in a rat α1 was sufficient to restore low $K^+$-induced Src activation.

Figure 3G:
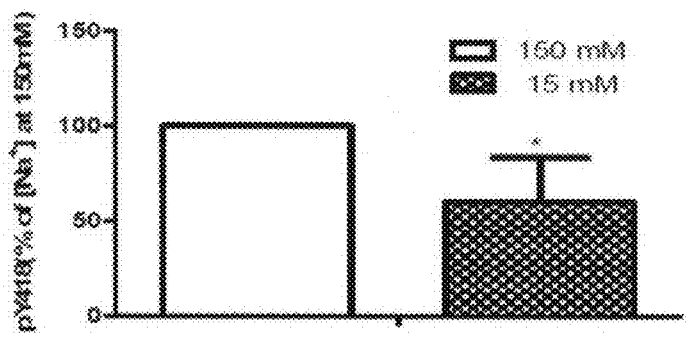
Figure 4:
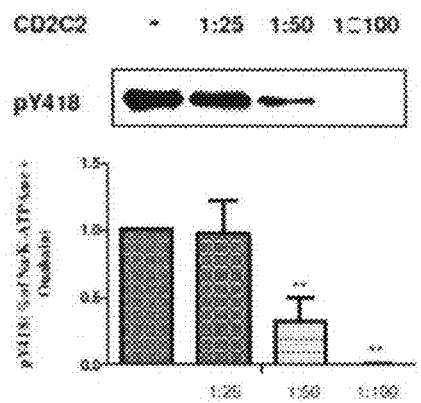
FIG. 4. CD2C2 peptide as a potent ouabain antagonist. CD2C2 peptide was incubated with purified Src (the amount was indicated as molar ratio of Src/Cd2C2) for 15 minutes in PBS solution. Then purified Na/K-ATPase from pig kidney was added for another 15 minutes. After that, ouabain was added to the reaction system for 5 minutes, followed by addition of 2 mM Mg2+/ATP. The Src activity was determined by Western blot probing with anti-phosphorylated Tyr418. A representative Western blot was shown, and quantitative data was presented as mean±S.E. of at 3 separate experiments. **, $p<0.01$.

To further confirm the ion-induced regulation of Na/K-ATPase/Src complex, the inventors also exposed the cells to low extracellular $Na^+$. Lowering the extracellular $Na^+$ would favor the formation of E1 Na/K-ATPase in live cells. Consistently, the inventors observed that decreasing $Na^+$ from 150 mM to 15 mM caused a further inhibition of cellular Src activity as depicted in FIG. 3G.

These findings now show that the formation of Na/K-ATPase/Src complex allows not only extracellular ouabain, but also the pump substrates to regulate Src and Src effectors. Several unique properties of this novel cellular signaling mechanism are worthy of note.

The formation of this receptor complex involves a unique pair of domain interactions. Specifically, the involvement of both A and N domains of the Na/K-ATPase in the interaction with Src kinase makes it possible for E2/E1 Na/K-ATPase to turn on/off the transducing activity of Src.

Also, the E1/E2 conformation-mediated signaling mechanism suggests that the Na/K-ATPase/Src complex can function as a receptor for both extracellular and intracellular ligands of the Na/K-ATPase.

Moreover, the ion-mediated regulation of receptor Na/K-ATPase/Src complex could also serve as a major mechanism by which the cell coordinates the pumping and leak activities across the plasma membrane because the activation/inhibition of protein kinases is essential for regulating the activity and trafficking of many membrane transporters. For example, hypokalemia activates Src in intact animals. Moreover, this activation appears to be responsible for reduced surface expression of ROMK in renal epithelial cells, contributing to renal preservation of $K^+$ under the $K^+$-restricted condition.

Finally, in addition to its substrates, many membrane and structural proteins as well as lipids interact with the Na/K-ATPase and regulate the formation of E1/E2 Na/K-ATPase. For example, the γ subunit increases the formation of E1-Na/K-ATPase. In addition, several naturally occurring mutants stabilize the pump in the E1 state. Thus, the normal operation of Na/K-ATPase/Src receptor complex may provide cells a vital mechanism to sensing both extracellular and intracellular cues, thus coordinating various cellular processes.

These studies now show that the association between the Na/K ATPase and Src involves two interacting pairs: one is between the ATPase second cytosolic domain (CD2) and Src SH2 domain. The other is between the ATPase nucleotide binding domain (N domain) and the Src kinase domain. While the simultaneous binding of both associating pairs keeps Src inactive, ouabain stimulation can disrupt the latter pair and release Src kinase from the N domain, triggering Src activation. The NaKtide derived from the N domain show potent inhibition of Src activity by interfering with the kinase domain conformation.

The new peptide from the CD2 domain (amino acid sequence: STNCV EGTAR GIVVY TGD [SEQ ID NO:1]), however, disrupts the interaction of the ATPase CD2/Src SH2 domain, and abolishes ouabain-induced Src stimulation. Thus, the peptides are more advantageous as specific ouabain antagonists, with less interference with cellular Src kinase activity by themselves. However, a combination of the compositions would be beneficial as well.

The present invention also provides assays for screening new chemicals that competitively inhibit the binding between CD2 and SH2, and antagonize ouabain stimulation.

EXAMPLES

Example 1

CD2 Method

Figure 5:
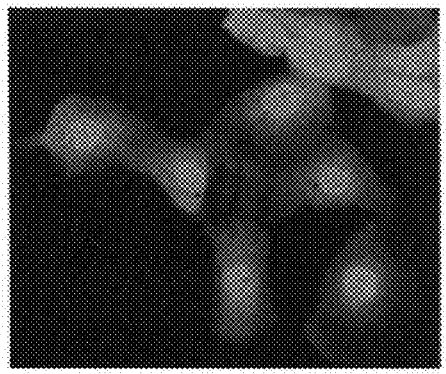
FIG. 5. Establishment of YFP and YFP-CD2 stable cell lines. The expression of YFP and YFP-CD2 is shown in clone YFP Ctrl and CD2-2 cell lines. The CD2 is from Pig Na/K ATPase (Swiss Prot ID P05024) amino acids-152-288 (Cytoplasmic domain 2).
Figure 5:
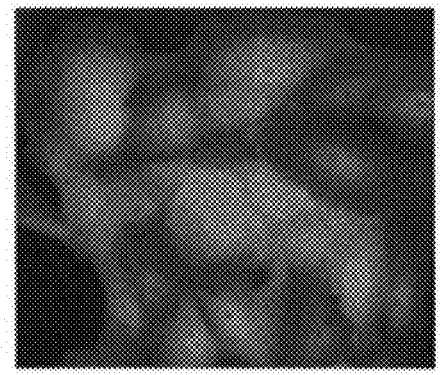
Figure 6:
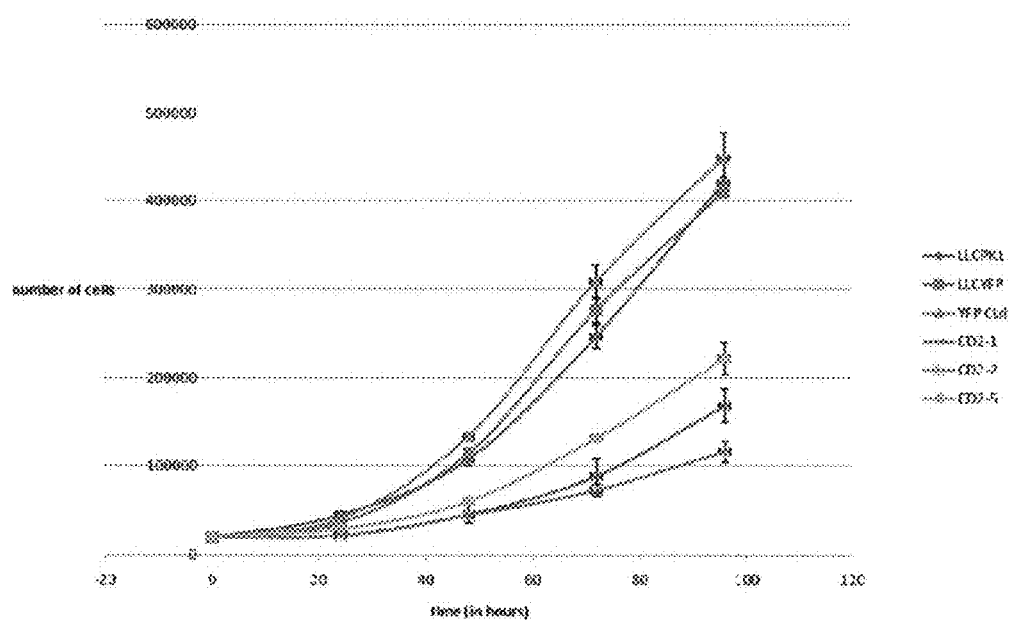
FIG. 6. Effects of expression of CD2 on cell growth. Control cell lines (LLC YFP and YFP Ctrl) and YFP-CD2 clones (CD2-1, CD2-2 and CD2-5). 20,000 cells were platted in 12 well plate format and cell number were counted using Trypan Blue staining with a Hemocytometer chamber for 24, 48, 72 and 96 hrs. Data is plotted as shown above (combination of 3 independent experiments, n=3).

The inventors showed that the Na/K-ATPase binds Src via two domains. The interaction between the nucleotide-binding domain of Na/K-ATPase with Src kinase domain inhibits Src activity whereas the interaction between second cytosolic domain of Na/K-ATPase α subunit (CD2) and Src SH2SH3 domain plays an important role in the formation of the receptor Na/K-ATPase/Src complex. To further test the significance of the latter interaction, the inventors have generated stable cell lines that expressing the YFP-fused CD2. FIG. 5 shows the expression of YFP and YFP-CD2 in two stable cell lines the inventors have generated. The sequence of CD2 is listed in the figure legend. Functionally, as depicted in FIG. 6, expression of YFP-CD2 caused a significant inhibition of cell growth, indicating that CD2 plays an important role in the formation of receptor Na/K-ATPase and thus in the regulation of cell growth.

Figure 7A:
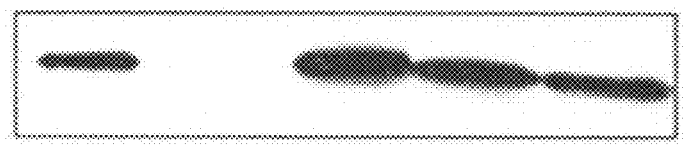
FIG. 7A, CD2C2 peptide attenuates the binding of CD2 to Src. CD2C2 was added to a mixture of Src and GST-CD2 at indicated concentrations. Src in the pull-down products was analyzed by Western blot with anti-Src antibody.
Figure 7B:
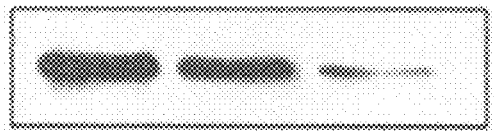
FIG. 7B, antagonizing ouabain-induced Src activation by CD2C2. Src was preincubated with indicated amount of CD2C2 peptide for 15 min in PBS. Then Na/K-ATPase purified from pig kidney was added for another 15 min. 1 μM ouabain was added to mixture for 5 min. Then Src autophosphorylation was detected in the presence of 2 mM ATP/Mg$^{2+}$. A representative blot from three independent experiments is shown.

Structural modeling suggests that the binding motif is likely at the C-terminus of CD2. To support this notion, the inventors checked whether the peptides derived from C-terminus of CD2 can attenuate the binding between CD2 and Src. Purified GST-CD2 was incubated with Src in the absence and presence of peptides for 15 min. Then pull-down pellets were analyzed by Western blot with antibody against Src. As shown in FIG. 7A, peptide CD2C2, but not CD2C1, was able to compete with and block the binding of GST-CD2 to Src SH2 domain. If CD2C2 peptide disrupts the SH2/CD2 interaction, the inventors expect that CD2C2 may abolish CTS-induced Src activation. To test that, the inventors preincubated Src with indicated amount of CD2 peptides for 15 min in PBS. Then purified pig kidney Na/K-ATPase was added for another 15 min. 1 μM ouabain was added to mixture for 5 min. Then Src autophosphorylation was detected in the presence of 2 mM ATP/Mg$^{2+}$. As shown in FIG. 7B, addition of CD2C2, but not CD2C1, to the mixture of purified Na/K-ATPase and Src, abolished ouabain-induced Src activation in a dose-dependent manner. Therefore, to search for new antagonists, the inventors will perform the following four sets of experiments.

First, the inventors will adapt a structure-based approach to look for CD2C2 mimetic. The inventors will synthesize smaller peptides and evaluate their potency as CTS antagonists. Structural information of CD2C2 derivatives will be generated according to the available Na/K-ATPase 3D structure (PDB ID: 2ZXE). Then the DOCK program will be used to search the NCI 3D structure database of more than 400,000 small molecules. Candidate compounds will be requested from the NCI. Their activities as CIS antagonists will be evaluated. Second, the inventors will develop a high throughput assay using an ELISA format to search chemical libraries for compounds that block ouabain-induced Src activation. Third, a FRET-based assay will be established to confirm whether the antagonist (positive hits from the above study) targets CD2/SH2. Briefly, CD2 and His-SH2SH3 will be expressed and purified. The purified proteins will be chemically labeled with a FRET fluorophore pair by targeting the available cysteine residues present in both CD2 and SH2. To validate the FRET assay, the inventors will test the FRET efficiency between, for example, 488-CD2 and 568-SH2SH3, and assess whether the CD2C2 peptide can reduce the FRED efficiency. CD2C1 will be used as a negative control. Needless to say, if the number of positive hits is limited, the inventors could simply test the effect of these compounds on CD2/SH2 interaction using the pull-down assay as in FIG. 7A. Fourth, because a positive hit could also be a Src inhibitor or target to the Src kinase domain/N domain interaction or prevent the binding of ouabain to the receptor Na/k-ATPase, the inventors will test these possibilities with the compounds that do not affect the interaction between the CD2 and SH2 domains.

Example 2

The inventors incubated the test chemicals with commercially available purified Src for 15 minutes in PBS solution. Then, purified Na/K ATPase from pig kidney was added for another 15 minutes. After that, ouabain was added to the reaction system for five minutes, followed by addition of 2 mM Mg2+/ATP. The Src activity was determined by Western blot probing with anti-phosphorylated Tyr418. Ouabain treated Na/K ATPase/Src complex was used as a positive control. The potential ouabain antagonist was identified if it inhibited Src activation under ouabain-inducing conditions. To further determine the specific inhibition of the binding between CD2/SH2, a FRET pair of CD2 and SH2 was designed. CD2 was labeled with Cy3, and SH2 was labeled with Cy5. Both peptides were incubated in a 96 well plate, and the FRET energy transfer was measured using a spectra meter. The chemicals which abolished the FRET energy transfer were identified as ouabain antagonists/inhibitors of CD2/SH2 interactions. These are cardiotonic steroid antagonists in general.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

The publication and other material used herein to illuminate the invention or provide additional details respecting the practice of the invention, are incorporated be reference herein, and for convenience are provided in the following bibliography. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

---

---

We claim:

1. A composition of matter comprising an amino acid compound consisting of the sequence STNCV EGTAR GIVVY TGD [SEQ ID NO: 1].

2. The composition of claim 1, which further comprises a therapeutically acceptable excipient.

3. The composition of claim 1, wherein the composition is capable of antagonizing a cardiotonic steroid (CTS-induced protein kinase cascade, upon administration to the patient.

* * * * *

UNITED STATES PATENT AND TRADEMARK OFFICE
CERTIFICATE OF CORRECTION

PATENT NO. : 8,691,947 B2  
APPLICATION NO. : 13/521871  
DATED : April 8, 2014  
INVENTOR(S) : Zi-Jian Xie, Qiqi Ye and Zhichuan Li Page 1 of 1

It is certified that error appears in the above-identified patent and that said Letters Patent is hereby corrected as shown below:

In the Claims

Column 12, Claim 2, Line 64, delete "(CTS-induced" and insert --(CTS)-induced--.

Signed and Sealed this
First Day of July, 2014

Michelle K. Lee
*Deputy Director of the United States Patent and Trademark Office*

SEQUENCE LISTING

```
<160> NUMBER OF SEQ ID NOS: 1

<210> SEQ ID NO 1
<211> LENGTH: 18
<212> TYPE: PRT
<213> ORGANISM: Sus scrofa

<400> SEQUENCE: 1

Ser Thr Asn Cys Val Glu Gly Thr Ala Arg Gly Ile Val Val Tyr Thr
1               5                   10                  15

Gly Asp
```